(12) United States Patent
Merlino (10) Patent No.: US 8,962,050 B2
(45) Date of Patent: Feb. 24, 2015

(54) HOOP CONTAINER DISPENSER

(76) Inventor: Domenick Merlino, Yonkers, NY (US)

(*) Notice: Subject to any disclaimer, the term of this patent is extended or adjusted under 35 U.S.C. 154(b) by 891 days.

(21) Appl. No.: 11/968,263

(22) Filed: Jan. 2, 2008

(65) Prior Publication Data

US 2008/0164181 A1 Jul. 10, 2008

Related U.S. Application Data

(60) Provisional application No. 60/883,397, filed on Jan. 4, 2007.

(51) Int. Cl.
| | | |
|---|---|---|
| *A23G 3/50* | (2006.01) | |
| *A61B 19/00* | (2006.01) | |
| *B65D 81/36* | (2006.01) | |
| *B65D 85/60* | (2006.01) | |

(52) U.S. Cl.
CPC .............. *A61B 19/00* (2013.01); *A63B 2225/68* (2013.01); *A63B 2225/687* (2013.01); *B65D 81/36* (2013.01); *B65D 81/363* (2013.01); *B65D 85/60* (2013.01)
USPC ............ 426/104; 426/115; 426/112; 426/106; 426/394; 446/76; 446/75; 446/386; 206/407

(58) Field of Classification Search
CPC ........ A44C 5/003; A63H 33/02; B65D 37/00; B65D 83/04; B65D 81/365; B65D 85/60; A63B 19/00; A63B 2208/12; A45F 3/16
USPC .......................... 426/104, 112, 106, 115, 134; 446/26–28, 71–73, 75–76, 386; 206/407
See application file for complete search history.

(56) References Cited

U.S. PATENT DOCUMENTS

| | | | | |
|---|---|---|---|---|
| 3,138,249 A | * | 6/1964 | Paulini | 116/2 |
| 3,332,166 A | * | 7/1967 | Alexander | 446/431 |
| 3,918,708 A | * | 11/1975 | Augusta | 472/72 |
| 4,768,688 A | * | 9/1988 | Harrigan | 224/148.2 |
| 4,938,477 A | * | 7/1990 | Kuervers | 482/105 |
| 5,323,554 A | * | 6/1994 | MacDonald | 40/633 |
| 5,338,244 A | * | 8/1994 | Huang | 446/242 |
| 5,622,293 A | * | 4/1997 | LeFevre | 224/148.2 |
| 5,779,095 A | * | 7/1998 | Diamond | 221/263 |
| 5,782,107 A | * | 7/1998 | Glanz | 63/3 |

(Continued)

OTHER PUBLICATIONS

Smarties Candy Necklace. Feb. 7, 2005. http://smartiesstore.com.*

(Continued)

*Primary Examiner* — Drew Becker
*Assistant Examiner* — Luana Z Long
(74) *Attorney, Agent, or Firm* — Westerman, Hattori, Daniels & Adrian, LLP (57) ABSTRACT

A container for holding novelty items, toys or candies that is an openable closed-shape with a lock/release plug. The closed-shape can be repeatedly opened and closed to remove and refill the novelty items. The container can be any closed-shape required for end use. A lock/release plug is used to both open and lock the closed-shape into a closed state. The lock/release plug is dimensioned to fit within the interior diameter of the closed-shape. The closed-shape has slots proximate each open end that interact with compression tabs on the lock/release plug. A center stop assists in aligning the compression tabs with the slots. The container can be configured to be a hula hoop or be adorned on one's body, such as a necklace or a bracelet.

22 Claims, 4 Drawing Sheets

(56) References Cited

U.S. PATENT DOCUMENTS

| | | | | |
|---|---|---|---|---|
| 5,887,448 | A * | 3/1999 | Gilbert et al. | 63/1.16 |
| 6,450,854 | B1 * | 9/2002 | Fireman et al. | 446/236 |
| 6,581,811 | B1 * | 6/2003 | Schillaci | 224/148.2 |
| 6,966,814 | B2 * | 11/2005 | Mendel | 446/236 |
| 7,303,458 | B1 * | 12/2007 | Wolfinbarger | 446/236 |

OTHER PUBLICATIONS

How Products Are Made: Hula Hoop (Jan. 2006): http://web.archive.org/web/20060127012844/http://www.madehow.com/Volume-6/Hula-Hoop.html.*

Pixy Stix: Candy You Ate As a Kid (Jan. 2005): http://web.archive.org/web/20050105092555/http://www.oldtimecandy.com/pixy-stix.htm.*

* cited by examiner

HOOP CONTAINER DISPENSER

BACKGROUND

1. Field of the Invention

The present invention relates generally to a unique form of packaging. In some examples, the packaging can function concurrently as a toy or can become a toy once the consumables are used. In some examples, the dispenser can be formed from an elongated tube having a cross-section that is any desired shape, in which the tube is filled with items such as, e.g., candy, toys, and/or other items.

2. Background Discussion

In this disclosure, the terminology "closed-shape" is used to describe shapes which start and end at substantially the same starting and ending points, including, e.g., shapes with any number of sides and any size or shape of said sides, including n-gons (i.e., shapes having n number of sides) having infinite numbers of infinitely small sides, such as, e.g., circles, ovals, ellipses, and other rounded or curved shapes, as well as shapes with linear sides, such as, e.g., triangles, squares, trapezoids, etc., as well as assorted other shapes with curved, straight, and/or other shaped sides.

In the background, hoops (such as, e.g., hula hoops) and other hollow closed-shapes have been used as toys and games of skill for many years—from rolling a hoop by hitting it with a stick to the hula hoop, from ring toss games in which closed-shapes are tossed onto stakes from a distance, to infants stacking and matching closed-shapes as a learning tool.

Typically, due to the enclosed nature of such closed-shapes (e.g., starting and ending at the same point), such closed-shapes have been used in some contexts, but have not found desirable use in relation to, e.g., containers and packaging for items or articles. In container arts, packages and the like are typically formed from generally linear shapes having ends (e.g., tops and bottoms) to facilitate opening, filling, dispensing, etc., such as, e.g., a cylindrical container or the like.

Accordingly, in the existing art, closed-shapes have had limited use and desirability, and there is a need for improvements related to closed-shaped items.

BRIEF DESCRIPTION OF THE DRAWINGS

The advantages of the instant disclosure will become more apparent when read with the specification and the drawings, wherein.

SUMMARY

According to some embodiments, a container for novelty items, toys or candies comprises:
 a. an openable closed-shape, such as a cylindrical hoop; and
 b. a plurality of novelty items, toys or candies inside the closed-shape.

In some examples, the openable cylindrical hoop is extruded.

In some examples, a snap fit connection is included for both opening the container and separating said hoop from a closed state to a separated state.

In some examples, the container is filled with candies.

In some examples, the container is a hula hoop.

In some examples, the container is configured to be adorned on one's body.

In some examples, the container is a necklace or a bracelet.

In some examples, a candy-filled hula-hoop is provided. The hoop has an extruded outer tube and an injection molded plug that snaps the ends together. The plug is openable so that the tube can then be unsnapped and kids can eat the candies, and then the tube can be re-closed.

In some embodiments, the extruded tube has two cutouts at each distal end, and a plug is provided that has two outward tangs that snap into the cutouts, and there is a central annular flange to abut the end of the tube to align the holes. Of course, this is merely one illustrative design and configurations can vary. In some examples, the plug is injection molded, while the tube is extruded and then cut.

In some examples, the tube can be filled with candies, toys and/or other items and things, like M&Ms, Hershey's Kisses, etc.

In some examples, the product can have a range of diameters. In some examples, sizes of tubes can include:
 1. Inside diameter of cavity cross-section of 0.25 inches, or 0.3 inches, or 0.4 inches, or 0.5 inches, or 0.75 inches or 1.0 inches or more (with outside diameter being slightly larger due to thickness of tube).
 2. Total diameter of the container can vary too (e.g., from about size of a bracelet in some examples to a hula-hoop diameter). Examples include diameters of 4 inches, 6 inches, 10 inches, 20 inches, 30 inches, 32 inch standard diameter, and from 24 to 36 diameter for normal hoop ranges.

In some examples, the extruded tube can be made more rigid to retain shape in, e.g., a hula-hoop usage while in other uses, it can be made flexible. For example, it can be made as a bracelet or a necklace. In bracelet or necklace examples, it can be flexible, such as to, e.g., facilitate hanging loosely or draping upon a person's neck or other body part.

In some embodiments, the material can preferably be very clear (e.g., similar to a plastic Poland Springs or the like water bottle—wherein, e.g., polyethylene terephthalate (PET) materials are typically used for that type of application and is safe with foods, etc.). In some embodiments, the candies or other items can be colorful and viewed through the material (i.e., such that the material can be translucent (e.g., largely see through) or substantially or completely clear or see through.

In some embodiments, the candies or other items can include pictures of various event-related-items for certain events or holidays, such as, e.g., small printing saying, e.g.: Happy Birthday; Happy Holidays; Merry Christmas; Get well soon; etc.

The snap fit can vary in other embodiments and can be designed to open and close the closed-shape or to simply open the closed-shape a single time without any re-closure capabilities. In some embodiments, one end can be fixedly adhered to the tube and the other openable and reclosable. Thus, a user can open and close the circular container as needed.

For hula hoop designs, in some embodiments, one of the snap fit portions is made large enough to push with one's thumb readily easily. The other side preferably is harder to press and maybe fixed more rigidly, or includes something surrounding it to prevent opening like a label, sticker or other covering.

In addition, for filling of the tube, the candies or other items can be in some examples, aligned in a row one-by-one, such that a single line of candies fills the tube. For example, the inside diameter can accommodate a row of circular hard candies, sized so as to fit inside the inner diameter—e.g., such that a diameter of the inside of the tube can be between about 1.1 and 1.9 times the diameter of the candies, or, preferably between about 1.2 to 1.8 times. Or, in some embodiments, within a range of about 1.1 to 1.4 times the diameter of the candies. In that manner, an orderly and necklace-like design can be presented. However, in contrast to a common necklace structure involving a string through the middle of the structure, the items are preferably aligned (and safely retained) inside a transparent or clear tube. Also, in some embodiments, the candies can be much smaller than the diameter of the tube.

In addition to (i.e., added in the same container) or as an alternative to candies, other items can be filled inside the container, such as, e.g., small toys for kids, like figurines, soldiers, cars, etc. For example, an exemplary configuration could be similar to a Christmas wreath filled with small toys and/or candies.

DETAILED DESCRIPTION OF THE INVENTION

In the preferred embodiments, a novel closed-shape container for the packaging of items having a small bulk items is provided. In some embodiments, the items can be edible, such as, e.g., candy, candy, popcorn, dried fruit, while in other embodiments, the items can be non-edible, such as jacks, balls, game disks, toys, etc. The packaging item, either after removal of the filler items or during storage of the fillers, retains its usability, becoming a toy, such as a hoop or jewelry such as a necklace or bracelet.

In preferred embodiments, a lock/release plug enables the closed-shape to be repeatedly opened and closed to emptying and refilling. The closed-shape can be used to "store" items, such as cereal for infants, while providing a toy both during storage and after. The closed-shape can be sold with its contents inside or in an empty condition, depending upon the end use and manufacturer's preference.

The closed-shapes can be of any size desired and can vary in overall diameter as well interior circumference. Although a circular hoop having a cylindrical cross-section is employed in some preferred embodiments, and is illustrated in the described figures, other closed-shape configurations and cross-sectional shapes thereof can also be used. For example, if the closed-shape is being used for a particular "goal", such as, e.g., tossing onto stakes, or another "goal" it can be any closed-shape suitable. Additionally, the cross-section of the poly can vary in shape and size depending upon use. The configuration is dependent upon the end use, ornamental shape desired, and other factors, and can be modified as desired by those skilled in the art. Additionally, the cross-sectional configuration of the closed-shape construction does not need to the same as the overall closed shape. For example, a circular closed shape can include, e.g. a square cross-sectional tubing that forms the circular closed-shape.

It is advantageous to define several terms before describing the preferred embodiments.

As explained above, for the purposes herein the term "closed-shape" shall define any geometric shape, including shapes with straight and/or curved sides or segments, including, e.g., polygons, circles, or any variation thereon (note: a circle is a polygon with an infinite number of sides).

Figure 1:
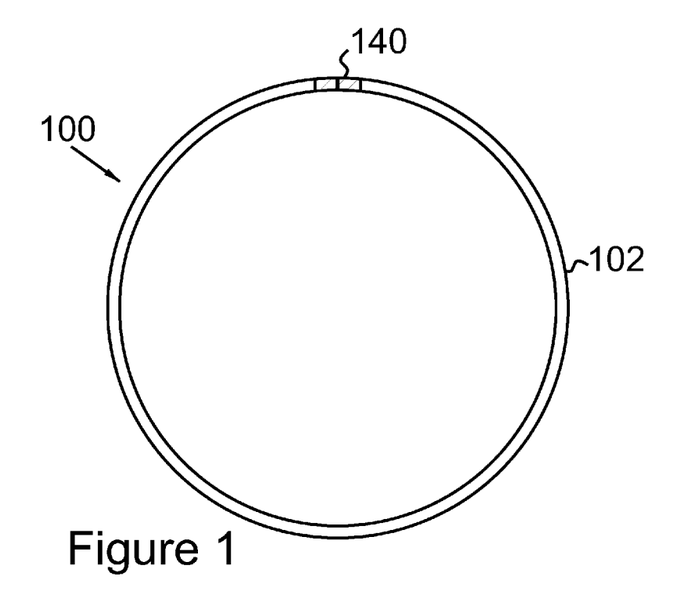
FIG. 1 is a top view of the fillable closed-shape in accordance with the present invention.

FIG. 1 illustrates the fillable closed-shape 100 in the configuration of a circle, or hoop, 102 with the lock/release plug 140 maintaining the hoop 102 in a closed position. The plug 140, described in more detail hereinafter, enables the hoop 102 to be opened and re-closed once the desired amount of the filler material has been removed. This enables the hoop 102 to be used as a storage device as well as an initial packaging device.

Figure 2:
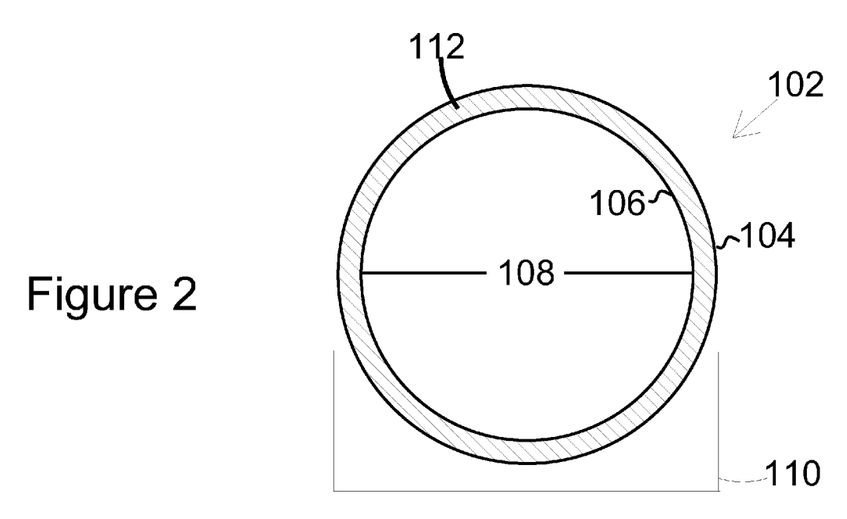
FIG. 2 is a cutaway end view of the interior of the fillable closed-shape in accordance with the present invention.

In FIG. 2, the hoop 102 has been cut and a cross section is illustrated showing the exterior diameter 110 of the exterior wall 104 of the hoop 102 in relation to the interior diameter 108 of the interior wall 106 of the hoop 102. The thickness between the exterior wall 104 and the interior wall 106 can vary depending upon the interior diameter 108 as well as the exterior diameter 110. For example, the interior fill space 112 can range from about 0.25 inches, to about 1.0 inch or more depending upon use. The thickness of the walls forming the closed-shape can be selected (e.g., increased/decreased appropriately) depending upon the thickness required for the end use. It should be noted that the description herein refers to an interior wall 106 and exterior wall 104 which, in a cylindrical configuration are the same. However, for ease of description and to include those embodiments that are not cylindrical, the outside portion of the hoop and inside portion will be referred to separately.

The exterior diameter 110 of the fillable closed-shape 100 can vary, e.g., from about size of a bracelet to a hula-hoop or even larger. The smaller exterior diameters, such as 4 inches or even 6 inches could be used for bracelets and other smaller items, while the progressively larger diameters, could be used for necklaces and other larger items. When used for hula hoops, the exterior diameters would normally be in the range from about 24 to 36 inches. The exact dimensions can be selected by those of skill in the art based on this disclosure based on the desired end use.

Figure 3:
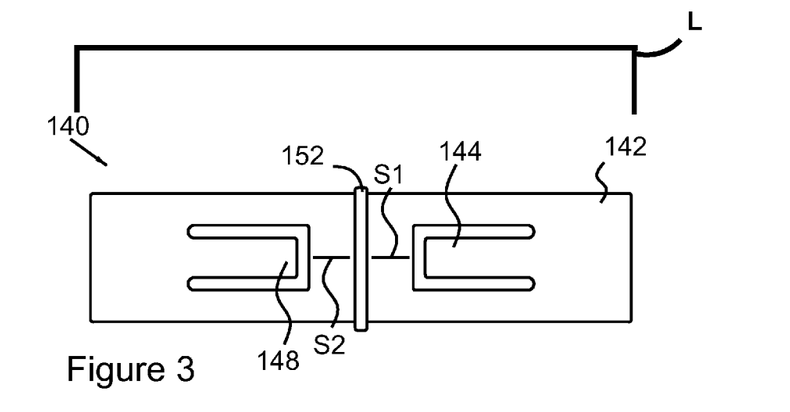
FIG. 3 is a top view of the lock/release button in accordance with the present invention.
Figure 4:
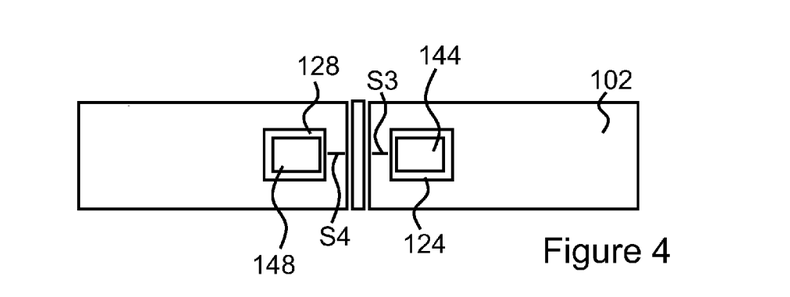
FIG. 4 is a top view of the lock/release button within the hoop in accordance with the present invention.
Figure 5:
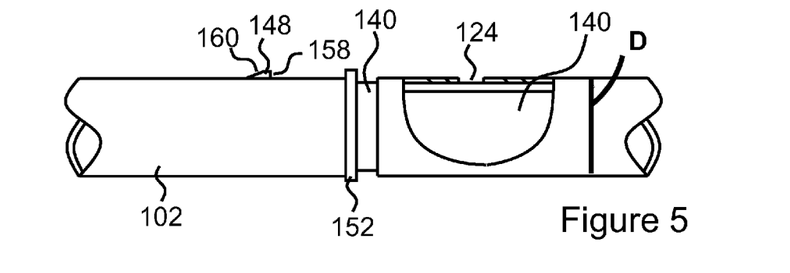
FIG. 5 is a partial cutaway side view of the lock/release button within the hoop with one side fully inserted and the other side of the hoop partially inserted in accordance with the present invention.

To maintain the interior fillable portion 112 of the closed-shape 100 in the closed position a lock/release plug 140 is used, as illustrated in FIGS. 3-5. The lock/release plug 140 has compression tabs 144 and 148 that are raised above the outer diameter D of the plug 140 and can be pressed to the plane of the diameter D or below. The compression tabs 144 and 148 can operate as would be understood based on this disclosure. For example, if the flexible closed-shape 100 is going to be tossed, the lock/release plug 140 and compression tabs 144 and 148 should be as lightweight as possible to prevent unbalancing the closed-shape 100. In addition, in some embodiments, the tabs 144 and 148 do not compress or vary in shape significantly, but the tube 102 itself snaps over the tabs—i.e., with the tube 102 flexing to accommodate the tabs 144 and 148.

The example lock/release plug 140 illustrated herein has a center stop 152 that is slight raised above the periphery of the body 142 to position the slots 124 and 128 located at the ends of hoop 102. The spacing S1 and S2 between the edge of the center stop 125 and the proximal edge of the compression tab 144 and 148 is notable as it needs to align with the slots 124 and 128 described hereinafter. The length L of the lock/release plug 140 is dependent upon the configuration of the fillable closed-shape 100. The length L of the lock/release plug 140 should not be so great that distorts the hoop 102 while still securely maintaining the hoop 102 together.

The interaction between the hoop 102 and the lock/release plug 140 is facilitated through the use of slots 124 and 128 within the hoop 102 as illustrated in FIG. 4. The slots 124 and 128 are dimensioned to be directly over the compression areas 144 and 148 of the lock/release plug 140. The spacing S1 between the center stop 152 and the compression tab 144 must be slightly greater than the spacing S3 between the edge of the hoop 102 and the proximal edge of the slot 124. Likewise, the spacing S2 between the center stop 152 and the compression tab 148 must be slightly greater than the spacing S4 between the edge of the hoop 102 and the proximal edge of the slot 128.

Figure 6:
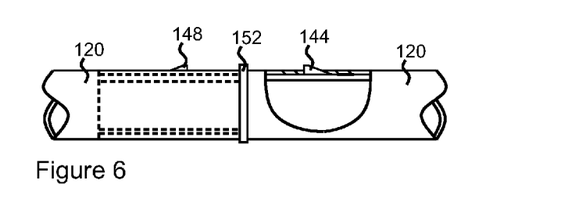
FIG. 6 is a cutaway side view of the lock/release button fully inserted within the hoop in accordance with the present invention.

The insertion of the lock/release plug 140 is illustrated in FIGS. 5 and 6. In FIG. 5, one end of the hoop 102 has been fully inserted over the lock/release plug 140. As seen, the compression tab 148 extends above the hoop 102 with the flat surface 158 proximal the edge of the hoop 102 and the angled surface 160 distal the open edge of the hoop 102. This configuration prevents the hoop 102 from being pulled off the lock/release plug 140 without depression of the compression tab 148. The angled surface 160 further enables the open edge of the hoop 102 to compress the compression tab 148 as it is slid onto the lock/release plug 140. The flat surface 158 is dimensioned, as noted heretofore, to sit adjacent to the proximal edge of the slot 128, thereby preventing separation of the hoop 102 from the lock/release plug 140. In this figure, the opposing open edge of the hoop 120 has not been slid onto the lock/release plug 140 a sufficient distance to enable the compression tab 144 to interact with the slot 124. In FIG. 6, both open edges of the hoop 120 have been fully inserted and brought adjacent to the center stop 152 and both compression tabs 148 and 144 are exposed, locking the hoop 102 together.

Figure 7:
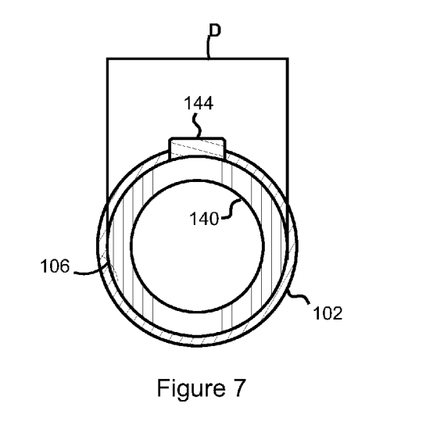
FIG. 7 is a cutaway end view of the lock/release button within the hoop in accordance with the present invention.

As seen in FIG. 7, the diameter D of the lock/release plug 140 should be slight less than that of the interior diameter 106 of the hoop 102 to enable the plug 140 to slide within the hoop 102. The compression tab 144 is seen slightly raised above the exterior diameter 104 of the hoop 102.

While an illustrative and preferred locking mechanism is shown and described herein, it is contemplated that other types of locking mechanisms could be employed in other embodiments. In that regard, in other embodiments, any type of clasp, buckle (such as, e.g., similar to a belt buckle), clip, clamp, snap-mechanism (e.g., similar to buttons on pants) or other mechanical engagement mechanism can be employed. Preferably, such mechanical engagement mechanisms can be opened, closed, and re-opened and re-closed numerous times.

Open-Shaped Storage/Display Embodiments

In some embodiments, the closed-shaped devices as described herein can be initially provided in an open-shaped configuration or arrangement (such as, e.g., during shipping to a retail or merchant location and/or during display and sale of the devices at the retail or merchant location). Among other things, providing the device in this configuration during transport, storage and/or display can have a variety of very significant advantages and costs savings. For example, closed-shapes (such as, e.g., hula hoops) take up a substantial amount of space due to their enclosing nature. Thus, by eliminating their enclosing nature during transport, storage and/or display, the shapes take up much less space. With the present construction, upon sale or at some other desired time, the shapes can be readily snapped or otherwise connected to form such a closed-shape. In situations in which goods are initially retained inside the containers, the ends could include removable paper, plastic and/or other covering material to retain product therein that is removed to effect closure. Of course, in preferred embodiments (as with the foregoing embodiments), only one end is fully opened to the interior such that product cannot fall out of both ends upon separating of the ends (i.e., such as to ensure that the product is manageable by a user).

Thus, in some preferred embodiments a new way of shipping hula hoops in straight lengths is provided that includes providing a connecting plug at one end. Here, the invention does not require that candies or other items be retained in the hoops. This feature provides yet a further simplification (and cost reduction) over the already simple and low cost hula hoop product. With the present invention, it is very easy for a consumer or a store owner to assemble the product—e.g., just bending the hoop and snapping it together. Thus, this provides a hole new approach to the hula hoop.

Among other things, this latter embodiment of the invention can provide the following and other benefits:

1. Reduced shipping costs. For example, on a standard 40 ft container, a regular carton containing pre-assembled 27" hoops, with 48 pieces per box, the carton size would be approximately 30"×12"×30" and one could fit about 480 palletized cartons per container, resulting in about 23,040 hoops. However, employing the new straight shipping carton (6"×85"×5") with the same 48 pieces, one could fit 1440 palletized cartons per container resulting in about 69,120 hoops (i.e., about 3 times as much product shipped).
2. Reduced retail space. Customer can display the same quantity of hoops using less than ⅓ of the valuable floor space that the conventional hoop carton would use. Moreover, product can readily be displayed and managed within a store (e.g., avoiding a more cumbersome shape of the closed-shape configuration during display)
3. Cost Effective to Drop Ship. The item can now be shipped via common carrier directly to the customer—i.e., thus, saving the customer an excessive "over-sized carton" shipping charge. For example, the UPS charge to ship one of the new "straight cartons" of hoops from N.Y. to Chicago would cost about $10.00 less than if someone shipped one standard carton to the same location.
4. Distribution. Hoops can now easily be distributed to other outlets as a result of the ease of storage and the effortless transportation of the "straight hoop carton". For example, it will be easier to distribute to charity events, the carnival industry, street vendors and even circuses.

Figure 8:
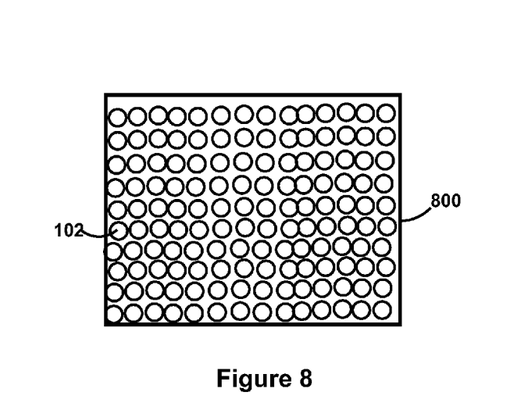
FIG. 8 is a cutaway end view of multiple hoops within a packing box in accordance with the present invention.

In addition to enabling the hoop 102 to be fillable, the use of the plug 140 provides shipping advantages. By enabling the hoop 102, or other closed-shape, to be disconnected and laid straight, the hoops 102 can be shipped in standard boxes as straight lengths. When filled hoops, or closed-shapes, 102 are shipped flat, the plug 140 as described heretofore will serve as the closure for one end and additional plug will be required in the open end to prevent the contents from spilling. The additional can be any type of plug known in the art as it will only serve to prevent spillage. As see in FIG. 8, the straight lengths can be stacked upon one another within the container 800, enabling multiple hoops 102 to be shipped within a substantially smaller space than circular, or other closed-shaped, hoops.

Figure 9:
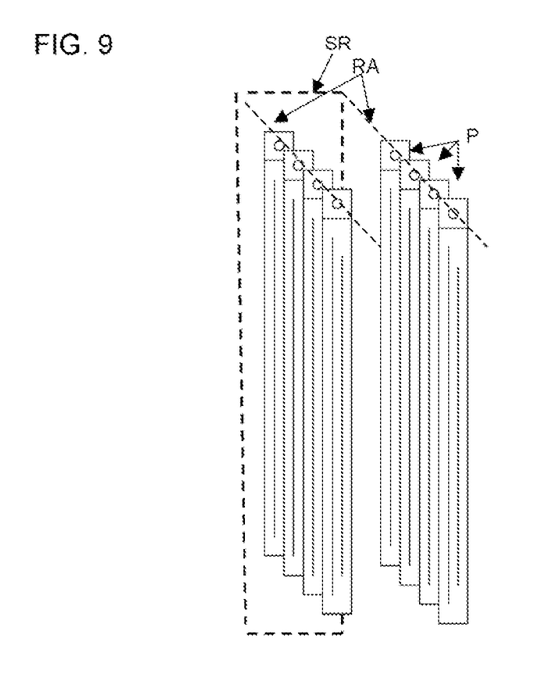
FIG. 9 is a side view of closed shape products on display within a retail establishment in an open-shaped configuration, with a substantially vertical display orientation.

In addition, FIG. 9 shows a some illustrative closed-shape products on display within a retail establishment in a open-shaped configuration, with a substantially vertical display orientation. As shown, the products P can be disposed neatly in rack R or the like (such as, e.g., along a wall or isle or even on a sales counter (e.g., for smaller products such as, e.g., small candy filled bracelet size or necklace size products) having retaining arms A that extend through supporting holes H formed in an upstanding tag portion T (e.g., affixed to the closed-shape product or on a container sleeve [e.g., plastic sleeve] holding the closed shape product P).

The above method generally enables the hoops or closed-shapes to be more easily distributed, handled, displayed and/or stored while providing a unique novelty item.

Other Aspects:

The fillable closed-shape 100 can be formed using an appropriate material, such as, e.g., a food compatible plastic, such as, e.g., polyethylene terephthalate (PET). In some preferred embodiments, the product can be formed via extrusion of the tube. By way of example, in some embodiments, the material can be extruded using a virgin FDA approved polyethylene terephthalate (PET) or other appropriate material. For example, PET is commonly used to package food and non-food items and is lightweight, shatterproof and recyclable. Other materials can also be used as appropriate.

In some embodiments, the fillable closed-shape 100 can be opaque, solid or clear and can be imprinted with designs or greetings to allow for customization for holidays, such as Christmas, Halloween, Hanukkah, etc., or events, such as birthdays. Closed-shapes made from clear plastic, such as PET or other materials used commonly for common water bottles, would enable the user to readily see the contents. For example, a hula hoop filled with colorful candies would be fun to use and watch the candies move around the hoop. The flexibility of the material is dependent upon end use. When the fillable closed-shape 100 is being used for a belt, bracelet or necklace, the flexibility would obviously be substantially greater than that of a fillable closed-shape used for a hula hoop or ring toss.

The manufacture of the fillable closed-shape and the lock/release plug will be dependent upon the end use and the material of manufacture. Extrusion is an economical method of manufacturing the length of the closed-shape while injection molding could be used for the lock/release plug.

The criteria regarding manufacturing, flexibility, dimensioning and materials will be obvious to those skilled in the related arts.

In an illustrative example, the product can include about a 32 inch diameter hoop use as a toy, such as a hula hoop, would use a hoop 102 having a wall thickness of 0.08. The lock/release plug 140 would have a length L of about 3.16 inches and the compression tabs 144 and 148 would be raised from the outer diameter D about 0.0625 inch.

While the invention has been described in detail with reference to some preferred embodiments, it should be apparent to one skilled in the art that various changes and modifications can be made and equivalents employed, without departing from the present invention.

What is claimed is:

1. A releasable-and-reclosable hula hoop container for candies, comprising:
    an openable closed-shaped tubular container having opposite ends that releasably and reclosably connect together via a snap-fit mechanism having at least one tab that snap fits into at least one slot;
    a plurality of candies inside said container;
    wherein said openable closed shape container has a container body that is extruded;
    wherein in a closed state said container is configured as a hula hoop with an outer container diameter of between about 20 to 36 inches and with an inside cross-sectional diameter of at least about 0.5 inches;
    wherein said container is made of a substantially transparent or see-through material through which said candies are observable;
    wherein said material of said container is a substantially rigid material having sufficient flexibility to allow opening and reclosing of said container while maintaining a substantially circular configuration when in said closed state sufficient for use as a hula hoop;
    wherein said candies are aligned substantially in a row within said container body, wherein an inside diameter of said container body is not more than about 1.9 times a diameter of at least some of said candies, wherein said container is configured such that said candies move around said hoop during use, and wherein said candies are sequentially dispensed one-by-one through an opening at one of said ends in an open state;
    wherein said candies are colored;
    whereby movement of said aligned colored candies in a row around said hoop is observable through said container during use of said hula hoop as a hula hoop in said closed state and during sequential one-by-one dispensing of said candies from said hula hoop in said open state.

2. The container of claim 1, wherein said container is a hula hoop with a diameter of between 24 to 36 inches, and wherein said container is made with a clear, extruded plastic through which said candies are displayed.

3. The container of claim 1, wherein said candies include circular hard candies substantially aligned in a row within said container.

4. The container of claim 1, wherein said candies include chocolate candies substantially aligned in a row within said container.

5. A method of using the container of claim 1, including a) with said container in said closed state having a user use said container as a hula hoop around the user's body with said candies observable within said container and b) having said user open said container from said closed state and dispense at least one of said candies.

6. The method of claim 5, further including prior to having said user use said container as a hula hoop and having said user open said container, delivering said container in said open state, while extending linearly and filled with said candies, within a carton containing a plurality of similar filled containers extending linearly in parallel to said container.

7. A hoop-shape container for candies, comprising:
    an openable closed-shape container body, said openable closed-shape container body having a length, an exterior diameter and an interior diameter, with ends of said length being connected in a closed state and disconnected in an open state;
    a plurality of candies inside said openable closed-shape container body;
    further including a lock/release connector to separate said container from a closed state to a separated state for removal of said candies and to then return said container to a closed state;
    wherein said lock/release connector is mounted on the interior of said container body;
    wherein in said closed state, said container is hoop-shaped with a diameter of between about 20 to 36 inches;

wherein said container is made with a substantially clear or see-through, extruded plastic through which said candies are displayed;

wherein said material of said container is a substantially rigid material having sufficient flexibility to allow opening and reclosing of said container while maintaining a substantially circular configuration when in said closed state sufficient for use as a hula hoop;

wherein said candies are aligned substantially in a row within said container body, wherein an inside diameter of said container body is not more than about 1.9 times a diameter of at least some of said candies, wherein said container is configured such that said candies move around said hoop during use, and wherein said candies are sequentially dispensed one-by-one through an opening at one of said ends in said open state;

whereby movement of said aligned candies in a row around said hoop is observable through said container during use of said hula hoop as a hula hoop in said closed state and during sequential one-by-one dispensing of said candies from said hula hoop in said open state.

8. The container of claim 7, wherein said closed-shape container further comprises at least one slot through a periphery of the container, said at least one slot being proximate open ends of said length of said closed-shape container, and wherein said lock/release connector includes at least one finger actuated compression tab configured to extend within said at least one slot so as to releasably retain said container in said closed state.

9. The container of claim 7, wherein said candies include circular hard candies substantially aligned in a row within said container.

10. The container of claim 7, wherein said candies include chocolate candies substantially aligned in a row within said container.

11. A hoop-shape container for candies, comprising:
an openable closed-shape container body, said openable closed-shape container body having a length, an exterior diameter and an interior diameter, with ends of said length being connected in a closed state and disconnected in an open state;
a plurality of candies inside said openable closed-shape container body;
further including a lock/release connector to separate said container from a closed state to a separated open state for removal of said candies and to then return said container to a closed state;
wherein said lock/release connector is mounted on the interior of said container;
wherein said lock/release connector includes a lock/release plug for separating said closed-shape from a closed state to a separated state for removal of said candies and then returning said closed-shape to a closed state;
wherein said lock/release plug is dimensioned to fit within said interior diameter of said closed-shape;
wherein said material of said container is a substantially rigid material having sufficient flexibility to allow opening and reclosing of said container while maintaining a substantially circular configuration when in said closed state sufficient for use as a hula hoop with a hula-hoop sized outer diameter of at least 20 inches;
wherein said candies are circular hard candies that are aligned substantially in a row within said container body, wherein an inside diameter of said container body is not more than about 1.9 times a diameter of at least some of said circular hard candies, wherein said container is configured such that said circular hard candies move around said hoop during use, and wherein said candies are sequentially dispensed one-by-one through an opening at one of said ends in said open state;

wherein said candies are colored;

whereby movement of said aligned colored circular hard candies in a row around said hoop is observable through said container during use of said hula hoop as a hula hoop in said closed state and during sequential one-by-one dispensing of said circular hard candies from said hula hoop in said open state.

12. The container of claim 11, wherein said lock/release plug further comprises compression tabs, said compression tabs interacting with slots to lock said closed-shape onto and release said closed-shape container from said lock/release plug.

13. The container of said 12, further comprising a center stop on said lock/release plug.

14. The container of claim 11, wherein said container is a hula hoop having an outer container diameter of between about 24 to 36 inches.

15. A container assembly for candies, comprising:
an openable closed-shape container, said openable closed-shape container having a length, an exterior diameter and an interior diameter, with ends of said length being connected in a closed state such as to form a substantially rigid loop sufficient for use as a hula hoop with an external diameter of between about 20 to 36 inches in said closed state and disconnected in an open state and configured to be extendable generally linearly in said open state;
a plurality of candies inside said openable closed-shape container; and
wherein said closed-shape container is contained in a shipping package with said candies therein and with said container body in an open state along with a plurality of other like closed-shaped containers similarly in an open state and each of said like closed-shape containers arranged substantially parallel to one another side-by-said within said shipping package.

16. The container of claim 15, wherein:
said container is made with a clear, extruded plastic through which said candies are displayed.

17. The container of claim 16, wherein said container is a hula hoop in said closed state with a diameter of between about 24 to 36 inches.

18. A container for edible items, comprising:
a) an openable tubular hoop having first and second ends that are releasably connectable together;
b) a releasable snap-fit connector mechanism including at least one tab that fits into at least one slot to maintain said hoop in a closed state and that is releasable from said at least one slot to place said hoop in an open state to remove some of said items;
c) said container is hula-hoop shaped in said closed state with a hula-hoop sized diameter of at least 20 inches;
d) said releasable snap-fit connector mechanism exposes an interior of said container to release and dispense said edible items in said open state, and
e) said container is made with a clear or see-through plastic through which said edible items are displayed;
f) wherein said material of said container is a substantially rigid material having sufficient flexibility to allow opening and reclosing of said container while maintaining a substantially circular configuration when in said closed state sufficient for use as a hula hoop;
g) wherein said edible items are aligned substantially in a row within said container body, wherein an inside diameter of said container body is not more than about 1.9 times a diameter of said edible items, wherein said container is configured such that said edible items move around said hoop during use, and wherein said edible items are sequentially dispensed one-by-one through an opening at one of said first and second ends in said open state;

h) whereby movement of said aligned edible items in a row around said hoop is observable through said container during use of said hula hoop as a hula hoop in said closed state and during sequential one-by-one dispensing of said edible items from said hula hoop in said open state.

19. The container of claim 18, wherein said edible items are candies.

20. The container of claim 19, wherein said candies include circular candies.

21. A method of using the container of claim 18, including a) with said container in said closed state having a user use said container as a hula hoop around the user's body with said edible items observable within said container and b) having said user open said container from said closed state and dispense at least one of said edible items.

22. The method of claim 21, further including prior to having said user use said container as a hula hoop and having said user open said container, delivering said container in said open state, while extending linearly and filled with said edible items, within a carton containing a plurality of similar filled containers extending linearly in parallel to said container.

* * * * *